US006583088B1

(12) United States Patent
Andersch

(10) Patent No.: US 6,583,088 B1
(45) Date of Patent: Jun. 24, 2003

(54) USE OF SPINOSYNES AS SOIL INSECTICIDES

(75) Inventor: Wolfram Andersch, Bergisch Gladbach (DE)

(73) Assignees: Bayer Aktiengesellschaft, Leverkusen (DE); Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 09/700,674

(22) PCT Filed: May 14, 1999

(86) PCT No.: PCT/EP99/03318

§ 371 (c)(1),
(2), (4) Date: Nov. 17, 2000

(87) PCT Pub. No.: WO99/60856

PCT Pub. Date: Dec. 2, 1999

(30) Foreign Application Priority Data

May 26, 1998 (DE) .......................................... 198 23 397

(51) Int. Cl.[7] ......................... A01N 43/02; A01N 43/00
(52) U.S. Cl. ........................................ 504/140; 504/209
(58) Field of Search ..................... 514/450; 424/405; 504/140, 209

(56) References Cited

U.S. PATENT DOCUMENTS

| 5,362,634 A | * 11/1994 | Boeck et al. .................. 435/76 |
| 5,670,364 A |   9/1997  | Mynderse et al. ....... 435/252.1 |
| 5,670,486 A |   9/1997  | Mynderse et al. ............. 514/28 |
| 5,840,861 A |  11/1998  | Mynderse et al. ......... 536/16.8 |
| 6,001,981 A | * 12/1999 | DeAmicis et al. ........... 536/7.1 |

OTHER PUBLICATIONS

Dow Elanco Trade Magazine, Down to Earth, vol. 52, No. 1 (month unavailable), 1997, pp. 1–24, G. D. Thompson et al, "The Discovery of Saccharopolyspora Spinosa and a New Class of Insect Control Produces".

* cited by examiner

*Primary Examiner*—Alton Pryor
(74) *Attorney, Agent, or Firm*—Joseph C. Gil; John E. Mrozinski, Jr.; Richard E. L. Henderson

(57) ABSTRACT

The present invention relates to the use of spinosyns for treating seed and plant propagation material.

3 Claims, No Drawings

USE OF SPINOSYNES AS SOIL INSECTICIDES

This Application is a 371 of PCT/EP99/03318 filed May 14, 1999.

The present invention relates to the use of spinosyns, in particular for treating the soil, for treating seed or plant propagation material, and for drenching and irrigating plants.

It is known that spinosyns can be used for controlling insects (WO 97/00 265, WO 93/09 126, WO 94/20 518, U.S. Pat. No. 5,362,634).

It has now been found that spinosyns have systemic properties and that application via the soil or via plant irrigation is possible. They may also be used for treating seed and plant propagation material.

The spinosyns are known compounds. The fermentation product described in U.S. Pat. No. 5,362,634 (A 83543) is composed of a variety of compounds termed Spinosyn A, B, C and the like (cf. WO 97/00 265, WO 93/09 126 and WO 94/20 518). The spinosyns may be represented by the following formulae (I) and (II):

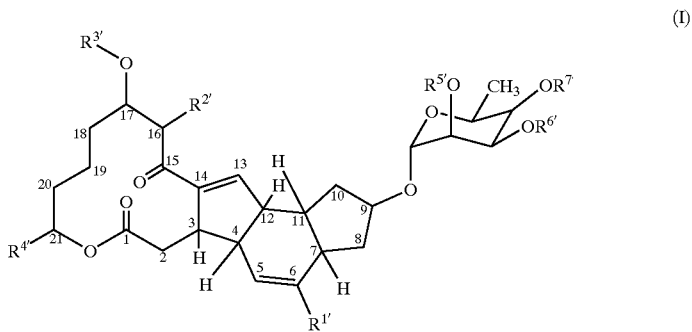

| Compound | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| Spinosyn A | H | $CH_3$ | $(CH_3)_2N$—sugar—$CH_3$ | $C_2H_5$ | $CH_3$ | $CH_3$ | $CH_3$ |
| Spinosyn B | H | $CH_3$ | $(CH_3)_2NH$—sugar—$CH_3$ | $C_2H_5$ | $CH_3$ | $CH_3$ | $CH_3$ |
| Spinosyn C | H | $CH_3$ | $H_2N$—sugar—$CH_3$ | $C_2H_5$ | $CH_3$ | $CH_3$ | $CH_3$ |
| Spinosyn D | $CH_3$ | $CH_3$ | $(CH_3)_2N$—sugar—$CH_3$ | $C_2H_5$ | $CH_3$ | $CH_3$ | $CH_3$ |
| Spinosyn E | H | $CH_3$ | $(CH_3)_2N$—sugar—$CH_3$ | $CH_3$ | $CH_3$ | $CH_3$ | $CH_3$ |
| Spinosyn F | H | H | $(CH_3)_2N$—sugar—$CH_3$ | $C_2H_5$ | $CH_3$ | $CH_3$ | $CH_3$ |
| Spinosyn G | H | $CH_3$ | $(CH_3)_2N$—sugar—$CH_3$ | $C_2H_5$ | $CH_3$ | $CH_3$ | $CH_3$ |
| Spinosyn H | H | $CH_3$ | $(CH_3)_2N$—sugar—$CH_3$ | $C_2H_5$ | H | $CH_3$ | $CH_3$ |

-continued $$(I)$$

[Structure of formula (I) showing a macrocyclic ring system with numbered positions 1-21, substituents $R^{2'}$, $R^{3'}O$ at position 17, $R^{4'}$ at position 21, $R^{1'}$ at position 6, and a sugar group with $R^{5'}O$, $OR^{6'}$, $OR^{7'}$, and $CH_3$ substituents attached via oxygen at position 9.]

| Compound | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| Spinosyn J | H | $CH_3$ | $(CH_3)_2N$–sugar (CH_3, O) | $C_2H_5$ | $CH_3$ | H | $CH_3$ |
| Spinosyn K | H | $CH_3$ | $(CH_3)_2N$–sugar (CH_3, O) | $C_2H_5$ | $CH_3$ | $CH_3$ | H |
| Spinosyn L | $CH_3$ | $CH_3$ | $(CH_3)_2N$–sugar (CH_3, O) | $C_2H_5$ | $CH_3$ | H | $CH_3$ |
| Spinosyn M | H | $CH_3$ | $(CH_3)_2NH$–sugar (CH_3, O) | $C_2H_5$ | $CH_3$ | H | $CH_3$ |
| Spinosyn N | $CH_3$ | $CH_3$ | $(CH_3)_2NH$–sugar (CH_3, O) | $C_2H_5$ | $CH_3$ | H | $CH_3$ |
| Spinosyn O | $CH_3$ | $CH_3$ | $(CH_3)_2N$–sugar (CH_3, O) | $C_2H_5$ | $CH_3$ | $CH_3$ | H |
| Spinosyn P | H | $CH_3$ | $(CH_3)_2N$–sugar (CH_3, O) | $C_2H_5$ | $CH_3$ | H | H |
| Spinosyn Q | $CH_3$ | $CH_3$ | $(CH_3)_2N$–sugar (CH_3, O) | $C_2H_5$ | H | $CH_3$ | $CH_3$ |
| Spinosyn R | H | $CH_3$ | $(CH_3)_2NH$–sugar (CH_3, O) | $C_2H_5$ | H | $CH_3$ | $CH_3$ |
| Spinosyn S | H | $CH_3$ | $(CH_3)_2N$–sugar (CH_3, O) | $CH_3$ | H | $CH_3$ | $CH_3$ |
| Spinosyn T | H | $CH_3$ | $(CH_3)_2N$–sugar (CH_3, O) | $C_2H_5$ | H | H | $CH_3$ |
| Spinosyn U | H | $CH_3$ | $(CH_3)_2N$–sugar (CH_3, O) | $C_2H_5$ | H | $CH_3$ | H |

-continued (I)

| Compound | R1' | R2' | R3' | R4' | R5' | R6' | R7' |
|---|---|---|---|---|---|---|---|
| Spinosyn V | CH₃ | CH₃ | (CH₃)₂N-sugar(CH₃) | C₂H₅ | H | CH₃ | H |
| Spinosyn W | CH₃ | CH₃ | (CH₃)₂N-sugar(CH₃) | C₂H₅ | CH₃ | H | H |
| Spinosyn Y | H | CH₃ | (CH₃)₂N-sugar(CH₃) | C₂H₅ | CH₃ | CH₃ | H |
| Spinosyn A 17-Psa | H | CH₃ | H | C₂H₅ | CH₃ | CH₃ | CH₃ |
| Spinosyn D 17-Psa | CH₃ | CH₃ | H | C₂H₅ | CH₃ | CH₃ | CH₃ |
| Spinosyn E 17-Psa | H | CH₃ | H | C₂H₅ | CH₃ | CH₃ | CH₃ |
| Spinosyn F 17-Psa | H | H | H | C₂H₅ | CH₃ | CH₃ | CH₃ |
| Spinosyn H 17-Psa | H | CH₃ | H | C₂H₅ | H | CH₃ | CH₃ |
| Spinosyn J 17-Psa | H | CH₃ | H | C₂H₅ | CH₃ | H | CH₃ |
| Spinosyn L 17-Psa | CH₃ | CH₃ | H | C₂H₅ | CH₃ | H | CH₃ | and (II)

| Compound | R1' | R2' | R3' | R4' | R5' |
|---|---|---|---|---|---|
| Spinosyn A 9-Psa | H | CH₃ | (CH₃)₂N-sugar(CH₃) | C₂H₅ | H |
| Spinosyn D 9-Psa | CH₃ | CH₃ | (CH₃)₂NH-sugar(CH₃) | C₂H₅ | H |

-continued

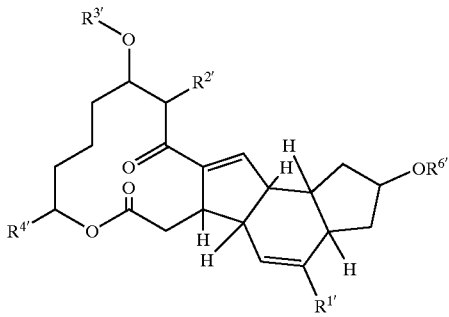

(II)

| Compound | $R^{1'}$ | $R^{2'}$ | $R^{3'}$ | $R^{4'}$ | $R^{5'}$ |
|---|---|---|---|---|---|
| Spinosyn A aglycone | H | $CH_3$ | H | $C_2H_5$ | H |
| Spinosyn D aglycone | $CH_3$ | $CH_3$ | H | $C_2H_5$ | H |

There have also been disclosed semisynthetic spinosyns of the formula (Ia)

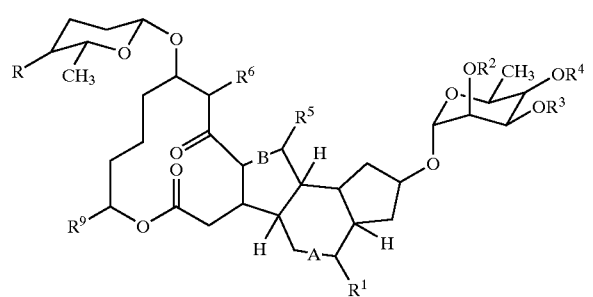

(Ia)

(WO 97/00 265) in which

A and B each represent a single bond, a double bond or an epoxide unit,

R represents

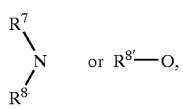

or $R^{8'}$—O, $R^1$ represents hydrogen or methyl, $R^2$, $R^3$ and $R^4$ independently of one another represent $C_1$–$C_4$-alkyl, $C_1$–$C_4$-halogenoalkyl, $C_1$–$C_4$-alkylcarbonyl or protected hydroxyl, $R^5$ represents hydrogen, $C_1$–$C_4$-alkyl, $C_1$–$C_4$-alkylamino or represents alkylhydroxylamino of the formula

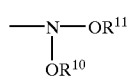

in which $R^{10}$ and $R^{11}$ independently of one another represent hydrogen, $C_1$–$C_4$-alkyl or $C_1$–$C_5$-alkylcarbonyl, $R^6$ represents hydrogen or methyl, $R^7$, $R^8$ and $R^{8'}$ independently of one another represent $C_1$–$C_4$-alkyl, $C_1$–$C_4$-halogenoalkyl or $C_1$–$C_4$-alkylcarbonyl, or represent protected amino, and $R^9$ represents methyl or ethyl.

The term "spinosyn" as used herein encompasses the compounds disclosed in WO 97/00 265.

Individual spinosyns, but also mixtures of the abovementioned spinosyns of the formulae (I), (Ia) and (II) may be used according to the invention.

Mixtures comprising at least one spinosyn of the formula (I) or (II) are preferably used.

Mixtures comprising a mixture of spinosyn A and spinosyn D in which the ratio of spinosin A to spinosyn D is generally between approximately 80:20 and approximately 98:2, a value of approximately 85:15 being preferred, are preferably used. Spinosad (see, for example, DowElanco trade magazine Down to Earth, Vol. 52, No. 1, 1997 and the literature cited therein), which comprises essentially a mixture of spinosyn A and spinosyn D in a ratio of approximately 85:15, is especially preferably used.

In particular, the fermentation product A 83543, which comprises approximately 85 to 90% of spinosyn A, approximately 10 to 15% of spinosyn D and minor amounts of spinosyns B, C, E, F, G, H and J and which is disclosed in U.S. Pat. No. 5,362,634, is used.

The acid addition salts described therein may also be used.

The following types of seed and plant propagation material are preferably treated according to the invention:

Maize, cereals (such as, for example, wheat, barley, oats, rye), rice, seed potatoes, cotton, oilseed rape, sunflower, beet (such as, for example, sugar beet), vegetable seed (such as, for example, onion, cabbage, tomato), (fodder) legumes, peanuts, soya, sorghum.

The following general treatment methods are preferably suitable for carrying out the seed treatment, or plant propagation material treatment, according to the invention:

dry treatments (preferably with addition of adhesion promoters such as, for example, liquid paraffin or talc), and, if appropriate, colorants, slurry treatments (preferably with addition of wetters, dispersants, emulsifiers, adhesives, inert fillers and colorants), aqueous liquid treatments (preferably with addition of emulsifiers, dispersants, thickeners, antifreeze agents, polymers, adhesives and colorants), solvent-based liquid treatments (with addition of solvents and colorants), emulsion treatments (with addition of emulsifiers, solvents and colorants).

The total active compound content in the spinosyn treatment formulations preferably amounts to 10 to 80% by weight.

Preferably, 1 to 300 g of active compound are applied to every 100 kg of seed or plant propagation material in the form of a treatment.

The treatment method according to the invention is carried out in customary treatment apparatuses or drum mixers as are customary, for example, in the construction industry.

Seed (or plant propagation material) and seed treatment formulation (or treatment formulation for plant propagation material) are mixed intimately in a conventionally used treatment apparatus.

After the seed (or plant propagation material) has been treated, it is dried to a sufficient degree in the case of the wet treatments, and the resulting treated seed (or plant propagation material) is then packaged in portions.

When applying the seed or plant propagation material which has been treated according to the invention, 1 to 5000 kg of treated seed (or plant propagation material) are generally employed per hectare of area under cultivation, preferably 100 to 300 kg of seed (or plant propagation material) per hectare of area under cultivation.

Surprisingly, it has been found that the spinosyns have systemic properties and, when applied via the soil, are very effective against the animal pests mentioned further below.

It is advantageous to apply granules comprising the active compound(s) into or onto the soil. Examples of suitable applications are broadcast, band, furrow and planting-hole application. Broadcast application is to be understood as superficial application of the active compound over the entire area to be treated and subsequent mechanical incorporation into the soil.

The use in seed boxes in rice cultivation may be mentioned especially (nursery box treatment).

It is particularly advantageous to emulsify or dissolve the spinosyns or their salts in water and to use this for irrigating the plants.

Examples of suitable applications are spraying onto the soil, drenching, i.e. irrigating the plants with active-compound-containing solutions, and drip irrigation, and also use in hydroponic systems, in particular in the production of vegetables and ornamentals.

The spinosyns may also be applied via the stem, for example by means of stem injection.

The seed treatments according to the invention are suitable for controlling animal pests, preferably arthropods and nematodes, in particular insects and arachnids, which are found in agriculture and in forests. They are effective against normally-sensitive and resistant species and against all or individual developmental stages. The abovementioned pests include:

From the order of the Isopoda, for example, Oniscus asellus, Armadillidium vulgare, Porcellio scaber.

From the order of the Diplopoda, for example, *Blaniulus guttulatus*.

From the order of the Chilopoda, for example, *Geophilus carpophagus*, Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis, Schistocerca gregaria*.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., *Pediculus humanus corporis*, Haematopinus spp., Linognathus spp.

From the order of the Mallophaga, for example, Trichodectes spp., Damalinea spp.

From the order of the Thysanoptera, for example, *Frankliniella occidentalis, Hercinothrips femoralis, Thrips palmi, Thrips tabaci*.

From the order of the Heteroptera, for example, Euryga-ster spp., *Dysdercus intermedius, Piesma quadrata, Cimex lectularius, Rhodnius prolixus*, Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana*, Cnaphalocerus spp.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis, Antho nomus* spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis, Costelytra zealandica, Oulema oryzae, Lissorhoptrus oryzophilus*.

From the order of the Hymenoptera, for example, Diprion spp., Hoplocampa spp., Lasius spp., *Monomorium pharaonis*, Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Liriomyza spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae, Tipula paludosa*.

From the order of the Siphonaptera, for example, *Xenopsylla cheopis*, Ceratophyllus spp.

From the order of the Arachnida, for example, *Scorpio maurus, Latrodectus mactans*.

From the order of the Acarina, for example, Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp.

On soil application, the spinosyns are distinguished by a potent insecticidal activity against the abovementioned pests.

Insects which can preferably be controlled with the aid of the treatment according to the invention are those of the following orders:

soil-dwelling insects: Diptera (for example the frit-fly, wheat-bulb fly), Coleoptera (for example Diabrotica (wire worm), Lepidoptera (for example dart moth), Blattophtheroidea, Myriopoda.

Leaf insects: Aphidina, Coleoptera, Brachycera, Lepidotera, Homoptera, Tysanoptera, Aleurodina, Cicadina, Acasi, Cossina, Heteroptera.

EXAMPLES

Example 1

Preparation of 20% Strength WS Formulations for Insecticidal Seed Treatment

"WS" means "water-dispersible powder for slurry seed treatment" and denotes a formulation type for seed treatment.

Formula: Carrier material (zero-formulation)

2.0% Brilliant Ponceau Red E RC 70

2.0% Helio Fast Ruby 4B 10

5.0% Baykanol SL 4.0% Ultrasil VN3 powder 1.5% Emulgator 1000 TR U, ground 0.8% Baysilone—Entschaumer E VM 30

84.7% Kaolin W

Procedure: 1 g of a 20% strength WS formulation is to be prepared.

Into agate mortars Ø 6.5 cm weigh 200 mg of active compound, add a suitable solvent (ACETONE), depending on the physical state of the material, dissolve and dry together with 800 mg of zero-formulation. After approx. 1–2 minutes, grind the product in a mortar until completely dry and package in product bottles.

Example 2

Limit Concentration/Soil-acting Insecticides

Test insect: *Diabrotica balteata*

Test plant: *Zea mays* (grain maize)

Dose:

4 g of ai/kg→200 mg (20% strength WS/10 g of seed)

2 g of ai/kg→100 mg (20% strength WS/10 g of seed)

1 g of ai/kg→50 mg (20% strength WS/10 g of seed)

Method: Weigh the particular amount of WS formulation stated into numbered round pots (Type 41, 90 ml) and disperse with 200, 100 or 80 µl of water. Add 10 g of maize seed. Treat the maize for approx. 1–2 min. on a test-tube shaker at setting 7 with the aid of a disposable spatula.

The maize is sown into numbered paraffin-treated cardboard pots (type 500, 0.5 1, height 83 mm, Ø at the top 110 mm) filled with 300 ml of BI-soil (standardized potting substrate, sandy loam). The soil is tamped down with a stamp (Ø 10 cm), 30 ml of water are poured on using a flask equipped with a rose, 5 maize kernels are introduced, the product is tamped down, filled up with 100 ml of BI soil and covered with glass lids (1 replication).

After 3 days, approx. 40 larvae (L2 instar) are counted into each pot. Also included are an untreated control with test animals and one without test animals (control) to assess the germinability of the maize seed.

After a further 7 days, the efficacy in % is determined. The efficacy is 100% if all maize plants have emerged.

Location temperature: 20° C.

Spinosad showed a good insecticidal action under the abovementioned conditions.

Example 3

Limit Concentration: Duration of Action/Root-systemic

Test insect: *Spodoptera frugiperda*

Test plant: *Zea mays* (grain maize)

Dose:

4 g of ai/kg→200 mg (20% strength WS/10 g of seed)

2 g of ai/kg→100 mg (20% strength WS/10 g of seed)

1 g of ai/kg→50 mg (20% strength WS/10 g of seed)

Method: Weigh the particular amount of WS formulation stated into numbered round pots (Type 41, 90 ml) and disperse with 200, 100 or 80 µl of water. Add 10 g of maize seed. Treat the maize for approx. 1–2 min. on a test-tube shaker at setting 7 with the aid of a disposable spatula.

The maize kernels are sown into numbered round pots (Ø 11 cm) filled with BI soil. Make 2 seed holes per pot, introduce 1 maize kernel per seed hole, cover and tamp down with a stamp (Ø 10 cm) (1 replication). Then drench and cover with film.

After 14, 21, 28 and 35 days, leaf material is excised from the plants for test purposes and placed into prepared Petri dishes (Greiner, Ø 9 cm). The dishes had previously been numbered and provided with a moistened (1.3 ml of water) filter paper disc (S+S round filter; Ø 8 cm; Ref.-No. 330 035) (1 replication).

Then, 6 Spodoptera larvae (L2 instar) are counted into the Petri dishes containing the maize leaves.

5–6 days after infection, the efficacy in % is determined in each case with reference to the control and the feeding profile.

Location temperature: 20° C.

Spinosad showed a good insecticidal action under the abovementioned conditions.

Example 4

Duration of Action/Root-systemic

Test insect: *Phaedon cochieariae* (larvae)

Test plant: *Brassica oleracea* (cabbage)

Dose:

2.0 g of ai/kg→20 mg (20% strength WS/2 g of seed)

1.0 g of ai/kg→10 mg (20% strength WS/2 g of seed)

0.5 g of ai/kg→5 mg (20% strength WS/2 g of seed)

Method: Weigh the particular amount of WS formulation stated into numbered round pots (Type 41, 90 ml) and disperse with 80 µl of water. Add 2 g of cabbage seed. Treat the cabbage seed for approx. 1–2 min. on a test-tube shaker at setting 7 with the aid of a disposable spatula.

The cabbage is sown into numbered round pots (Ø 11 cm) filled with BI soil. Create a seed furrow and place approx. 6 seeds in the middle of the pot over approx. 3 cm, close the seed furrow, tamp down with a stamp (Ø 10 cm) (7 replications). Then drench and cover with film.

After the cabbage plants have emerged, drill-jig sleeves (length 20 cm, Ø 5 cm) are placed on the pots, the upper edge being treated with talc (approx. 2 cm).

Approx. 10 Phaedon larvae are counted into the drill-jig sleeves at intervals of 7, 14, 21 and 28 days, only 2 pots being infected per week and concentration.

After 3–4 weeks in each case, the efficacy is determined in % with reference to the feeding profile.

Location temperature: 20° C.

Spinosad showed a good insecticidal action under the abovementioned conditions.

Example 5

Duration of Action/Soil-dwelling Insects

Test insect: *Hylemyia antiqua*
Test plant: *Allium cepa* (onion)
  Dose:
    2.0 g of ai/kg→20 mg (20% strength WS/2 g of seed)
    1.0 g of ai/kg→10 mg (20% strength WS/2 g of seed)
    0.5 g of ai/kg→5 mg (20% strength WS/2 g of seed)
  Method: Weigh the particular amount of WS formulation stated into numbered round pots (Type 41, 90 ml) and disperse with 80 µl of water. Add 2 g of onion seed. Treat the onion seed for approx. 1–2 min. on a test-tube shaker at setting 7 with the aid of a disposable spatula.

The onions are sown into numbered round pots (Ø 11 cm) filled with BI soil. Create a seed furrow and place approx. 30 seeds therein, tamp down and close the seed furrow, (3 replications). Then drench and cover with film.

After 3 and 5 weeks, the onion plants are infected at their base with Hylemyia eggs, using a hollow spatula (loosen soil surface beforehand).

10 days layer in each case, the efficacy in % is determined. The efficacy is 100% when no plant has been destroyed.

Location temperature: 20° C.

Spinosad showed a good insecticidal action under the abovementioned conditions.

Example 6

Limit Concentration—Root-systemic Action Against *Spodoptera Frugiperda*

Material and technical data:
  Plastic pots (250 ml)
  BI-soil comprising approx. 12% moisture
  Krefft mixer
  pregerminated maize (approx. age 3 days)
  transparent plastic tubes, diameter 5 cm/height 50 cm
  Spodoptera frugiperda Larvae (L2-3 instar)
  2 replications
Objective:
  To determine the limit concentration of test preparations in soil.
Method:
  Preparation of the laboratory formulation:
  The amount of active compound which corresponds to the application rate is dissolved in 5 ml of acetone+Emulgator PS 16 (4:1) and diluted with water to a 0.2% strength stock solution.

Experimental Set-up:
  The plastic pots are filled with BI soil. The appropriate amount of active compound solution is subsequently pipetted into the soil. The active compound and the soil are mixed for 10 seconds in the Krefft mixer at the highest speed. The soil is then filled into the pots and 3 pregerminated maize plants are placed on the bottom.

The pots are placed in the greenhouse at 20° C. and a relative atmospheric humidity of 70%. When the maize plants have reached a height of approx. 5 cm, transparent plastic tubes are placed over the plants and pushed into the soil surface. 1 week after the experiment has been set up, 7 Spodoptera frugiperda larvae are introduced per pot.
Evaluation:
  7 days after infection in each case, the efficacy is determined in % Abbott with reference to the control and the feeding profile.

Spinosad showed a good insecticidal action under the abovementioned conditions.

Example 7

Limit concentration—root-systemic Action Against *Plutella Xylostella* NS

Material and technical data:
  Plastic pots (250 ml)
  BI-soil comprising approx. 12% moisture
  Krefft mixer
  Savoy cabbage plants, approx. 3 weeks old
  Plutella xylostella NS larvae (instar 2-3)
  2 replications
Objective:
  To determine the limit concentration of test preparations in soil.
Method:
  Preparation of the laboratory formulation:
  The amount of active compound which corresponds to the application rate is dissolved in 5 ml of acetone+Emulgator PS16 (4:1) and diluted with water to a 0.2% strength stock solution.
Experimental Set-up:
  The plastic pots are filled with BI soil. The appropriate amount of active compound solution is subsequently pipetted into the soil. The active compound and the soil are mixed for 10 seconds in the Krefft mixer at the highest speed. The soil is then filled into the pots, and cabbage plants are planted.

The pots are placed in the greenhouse at 20° C. and a relative atmospheric humidity of 70%. One week after the experiment has been set up, the test plants are infected with Plutella xylostella larvae. To this end, 10 larvae are introduced into animal cages and clipped onto a young leaf.
Evaluation:
  3 days after infection in each case, the efficacy is determined in % Abbott with reference to the control and to the feeding profile.

Spinosad showed a good insecticidal action under the abovementioned conditions.

Example 8

Limit Concentration—Root-systemic Action Against Phaedon Cochleariae Larvae

Material and technical data:
  Plastic pots (250 ml)
  BI-soil comprising approx. 12% moisture Krefft mixer Savoy cabbage plants, approx. 3 weeks old Phaedon cochleariae larvae (instar 2-3)

2 replications

Objective:

To determine the limit concentration of test preparations in soil.

Method:

Preparation of the laboratory formulation:

The amount of active compound which corresponds to the application rate is dissolved in 5 ml of acetone+Emulgator PS16 (4:1) and diluted with water to a 0.2% strength stock solution.

Experimental Set-up:

The plastic pots are filled with BI soil. The appropriate amount of active compound solution is subsequently pipetted into the soil. The active compound and the soil are mixed for 10 seconds in the Krefft mixer at the highest speed. The soil is then filled into the pots, and cabbage plants are planted.

The pots are placed in the greenhouse at 20° C. and a relative atmospheric humidity of 70%. One week after the experiment has been set up, the test plants are infected with Phaedon cochleariae larvae. To this end, 10 larvae are introduced into animal cages and clipped onto a young leaf.

Evaluation:

3 days after infection in each case, the efficacy is determined in % Abbott with reference to the control and to the feeding profile.

Spinosad showed a good insecticidal action under the abovementioned conditions.

What is claimed is:

1. A method for combating at least one pest which attacks a plant, said at least one pest selected from the group consisting of *Melanoplus differentialls, Schistocerca gregaria, Forficula auricularia*, Reticulitermes spp., *Phylloxera vastatrix*, Pemphigus spp., Trichodectes spp., Damalinea spp;., *Frankliniella occidentalis, Hercinothrips femoralis, Thrips palmi, Thrips tabaci*, Eurygaster spp., *Dysdercus intermedius, Piesma quadrata, Rhodnius prolixus*, Triatoma spp., *Aleurodes brassicae, Bemisia tabaci, Trialeurodes vaporariorum, Aphis gossypii, Brevicoryne brassicae, Cryptomyzus ribis, Aphis fabae, Eriosoma lanigerum, Hyalopterus arundinis, Macrosiphum avenae*, Myzus spp., *Phorodon humuli, Rhopalosiphum padi*, Empoasca spp., *Euscelis bilobatus, Lecanium corni, Saissetia oleae, Laodelphax striatellus, Aonidiella aurantii, Aspidiotus hederae*, Pseudococcus spp., Psylla spp., *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella, Earias insulana, Mamestra brassicae, Panolis flammea, Prodenia litura, Trichoplusia ni, Carpocapsa pomonella*, Pieris spp., *Pyrausta nubilalis, Cacoecia podana, Capua reticulana, Choristoneura fumiferana, Clysia ambiguella, Homona magnanima, Tortrix viridana, Phaedon cochleariae, Psylliodes chrysocephala, Epilachna varivestis*, Antho nomus spp., *Cosmopolites sordidus, Ceuthorrhynchus assimilis, Hypera postica, Meligethes aeneus*, Diprion spp., Hoplocampa spp., *Oscinella frit, Pegomyia hyoscyami, Ceratitis capitata, Dacus oleae, Bryobia praetiosa*, and Panonychus spp., said method comprising exposing the root of the plant to one or more spinosyns.

2. A method for protecting a developing plant from at least one pest which attacks the plant, said at least one pest selected from the group consisting of *Melanoplus differentialis, Schistocerca gregaria, Forficula auricularia*, Reticulitermes spp. *Phylloxera vastatrix*, Pemphigus spp., Trichodectes spp., Damalinea spp., *Frankliniella occidentalis, Hercinothrips femoralis, Thrips palmi, Thrips tabaci*, Eurygaster spp., *Dysdercus intermedius, Piesma quadrata, Rhodnius prolixus*, Triatoma spp., *Aleurodes brassicae, Bemisia tabaci, Trialeurodes vaporariorum, Aphis gossypii, Brevicoryne brassicae, Cryptomyzus ribis, Aphis fabae, Eriosoma lanigerum, Hyalopterus arundinis, Macrosiphum avenae*, Myzus spp., *Phorodon humuli, Rhopalosiphum padi*, Empoasca spp., *Euscelis bilobatus, Lecanium corni, Saissetia oleae, Laodelphax striatellus, Aonidiella aurantii, Aspidiotus hederae*, Pseudococcus spp., Psylla spp., *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella, Earias insulana, Mamestra brassicae, Panolis flammea, Prodenia litura, Trichoplusia ni, Carpocapsa pomonella*, Pieris spp., *Pyrausta nubilalis, Cacoecia podana, Capua reticulana, Choristoneura fumiferana, Clysia ambiguella, Homona magnanima, Tortrix viridana, Phaedon cochleariae, Psylliodes chrysocephala, Epilachna varivestis*, Antho nomus spp., *Cosmopolites sordidus, Ceuthorrhynchus assimilis, Hypera postica, Meligethes aeneus*, Diprion spp., Hoplocampa spp., *Oscinelia frit, Pegomyia hyoscyami, Ceratitis capitata, Dacus oleae, Bryobia praetiosa*, and Panonychus spp., said method comprising treating the root of the developing seed of said plant with one or more spinosyns.

3. The method of claim 1 or 2, wherein the plant is selected from the group consisting of maize, cereal, rice, seed potato, cotton, oilseed rape, sunflower and vegetable seed.

* * * * *